United States Patent [19]

Mikkelsen

[11] Patent Number: Plant 5,920

[45] Date of Patent: Mar. 31, 1987

[54] IMPATIENS PLANT NAMED COMET

[75] Inventor: James C. Mikkelsen, Ashtabula, Ohio

[73] Assignee: Mikkelsens, Inc., Ashtabula, Ohio

[21] Appl. No.: 664,400

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab et al.

[57] ABSTRACT

An impatiens plant named Comet, having large deep pink to red purple flower color, large number of leaves in a whorl, multiple flowering at a leaf axil, good keeping quality of flowers, extremely floriferous, long internodes on a compact plant, terminal shoot that is slow to elongate, irregular lateral branching from the leaf whorl, and by its adaptability to various environments of use.

1 Drawing Figure

1

The present invention relates to a new and distinctive cultivar of New Guinea Impatiens plant, botanically known as Impatiens, and referred to by the cultivar name Comet.

Comet was developed by me in Ashtabula, Ohio, through controlled breeding by crossing Corona, disclosed in U.S. Plant Pat. No. 5,184 (seed parent)×Mikkelsen Seedling No. 82-MISC-1 (pollen parent). Asexual reproduction by terminal or stem cuttings taken in Ashtabula, Ohio, has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Larger, more vigorous growing plant than Solared, U.S. Plant Pat. No. 5,131. Similar in growth habit to Quasar, Columbia and Dawn. Quasar and Dawn are disclosed in my pending applications and Columbia is disclosed in U.S. Plant Pat. No. 5,126. Comet is more compact than Corona and Gemini, the latter being disclosed in U.S. Plant Pat. No. 5,132.

2. Flower color is deep pink to red purple and a shade deeper than Corona; color is more intense under winter conditions.

3. Flower size is larger than Columbia and Corona, similar in size to Gemini, but smaller than Zenith, disclosed in a pending application.

4. Flowers have excellent keeping qualities and nestle in the foliage as well as over the top, similar to Quasar and Pulsar, also disclosed in a pending application.

5. Leaf color is similar to Gemini and Pulsar but shows more midrib variegation than either, and Comet has a smaller leaf than Gemini.

6. Plants and flowers have good low temperature tolerance, continuing to grow and bloom after two (2) nights of 2.2° C. when planted outside in early May.

7. The new cultivar is self-branching, a vigorous grower and a compact mound in form with vigorous stems, all of which make it ideal for pots, hanging baskets and bedding plant use.

8. Flowering begins earlier than Corona and it has the multiple flowering habit per leaf axil that Pulsar and Quasar have. As leaf number increases in the whorl so does the flowering.

2

9. An excellent cultivar for further hybridization work for the multiple flowering characteristic on a compact plant for use as a pot plant or border plant.

10. The terminal shoot of branch does not elongate as fast as other New Guinea cultivars, as flowering from the node below the terminal may be well advanced before elongation occurs. Lateral branching is also unique as a leaf whorl may lateral branch before flower buds open or not until flowers have dropped from a leaf axil, which results in a compact plant with long internodes.

The accompanying colored photograph taken in March 1984 illustrates the overall appearance in perspective view of Comet, and showing the colors as true as it is reasonably possible to obtain in a colored reproduction of this type.

The following is a detailed description of my new impatiens cultivar based on plants produced under commercial practices in Ashtabula, Ohio, grown in 5.5" green plastic pots during the winter of 1983–1984, and describes colors under reduced sunlight and early floriferous flowering in an adverse environment. Color references are made to The Royal Horticultural Society Colour Chart except where general terms of ordinary dictionary significance are used.

Parentage: Corona×Mikkelsen Seedling No. 82-MISC-1.

Propagation:

(A) *Type cutting.*—Stem 15 mm long will develop 4 to 5 cm long in 18 to 21 days.

(B) *Time to root.*—8 to 10 days at 23° C. summer, 10 to 12 days at 20° C. winter.

(C) *Rooting habit.*—Large mass of fiberous roots from the stem.

Plant description:

(A) *Form.*—Symmetrically mounded, compact, flowering herb.

(B) *Habit of growth.*—Vigorous, self-branching, compact mounded, continuous flowering, light red stems.

(C) *Foliage description.*—Broad dark green foliage with purpling at edges and top, heavy variegation around the midrib. Veins are red in color. (1) Size: 7.5 to 8.5 cm long×3.0 to 3.25 cm wide. (2) Shape: Lanceolate to ovate with acuminate apex and acute base. (3) Texture: Rugose upper side, glabrous under side. (4) Margin: Serrated, finely ciliated. (5) Color: Young foliage, top side 146A, under side 183C. Mature foliage, top side 139A, under side 183A. (6) Venation: Pinnate with red midrib.

Flowering description:

(A) *Flowering habits.*—Flowers continuously from leaf whorl in a semi-progressively, semi-orderly manner (number of flowers vary from 1 to 3 per leaf axil); 5 to 7 days are required from buds showing color to bloom, and flowers last 2 to 3 weeks.

(B) *Natural flowering season.*—Indeterminant and continuous. Quantity of flowers increase with increasing levels of light intensity and duration.

(C) *Flower buds.*—Ellipsoidal, flowers perfect, reddish spur 3.75 to 4.0 cm long on mature bud with throat behind ovary and originating from the major sepal.

(D) *Flowers borne.*—On individual short pedicels from whorls of 10 or more leaves (17 leaves maximum counted in a whorl), increasing in number as plant matures, but not consistent on each branch; flowering semi-progressively around the whorl as leaves and buds develop (again inconsistent and ranged from 1 to 3 flowers per leaf axil). Flowers are from above to inside the leaf canopy.

(E) *Quantity of flowers.*—Very floriferous; can have 2 whorls on a stem blooming at the same time; flowering continuous so that tight buds to mature blooms are visible at the same time in large numbers.

(F) *Petals.*—(1) Shape: Heart shaped, top petal dominant, 4 others overlap and are symmetrical. (2) Color: top side in winter when opening 78B, fading to 77C-D; under side 77B fading to 77C; top petal has large oblong red area around the center ridge on the under side. (3) Number of petals: Five (5) in number. (4) Size of flowers: 6.0 to 7.0 cm.

(G) *Reproductive organs.*—(1) Stamens: five (5) in number. (a) Anther shape: Hooded, 67A. (b) Pollen color: Cream. (2) Pistels (a) Stigma shape: 5, segmented column, reddish in color. (b) Style color: Clear. (c) Ovaries: Five (5) in number, celled, 4 mm until fertilized, reddish green in color.

Disease resistance: No significant disease or insect problems have been seen to date.

Other important characteristics of new cultivar: 1. Number of leaves in a leaf whorl (10 or more). 2. Multiple flowering from leaf axil. 3. Terminal shoot does not elongate until flowering is well underway on the node below. 4. Long internodes on a compact plant. 5. Irregular lateral branching from leaf whorl; frequently there are lateral branches when flower buds in leaf axil, and lateral branches after flower buds drop from leaf axil.

I claim:

1. A new and distinct cultivar of New Guinea Impatiens plant named Comet, as described and illustrated, and particularly characterized by its large deep pink to red purple flower color, large number of leaves in a whorl, multiple flowering at a leaf axil, good keeping quality of flowers, extremely floriferous, long internodes on a compact plant, terminal shoot that is slow to elongate, irregular lateral branching from the leaf whorl, and by its adaptability to various environments of use.

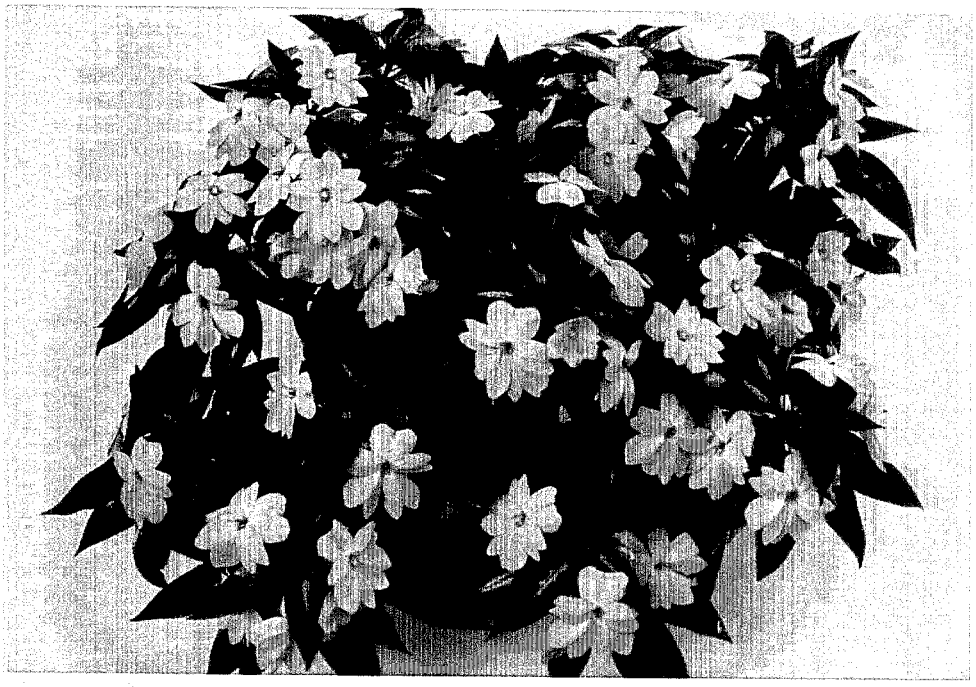

* * * * *